United States Patent [19]

Wieland

[11] 4,361,558
[45] Nov. 30, 1982

[54] HALOGENATED STEROIDS

[75] Inventor: Peter Wieland, Oberwil, Switzerland

[73] Assignee: Ciba-Geigy Corporation, Ardsley, N.Y.

[21] Appl. No.: 256,205

[22] Filed: Apr. 21, 1981

[30] Foreign Application Priority Data

Apr. 29, 1980 [CH] Switzerland .................. 3303/80

[51] Int. Cl.³ .............................. A61K 31/56
[52] U.S. Cl. ................... 424/243; 260/397.45
[58] Field of Search ............... 260/397.45; 424/243

[56] References Cited

U.S. PATENT DOCUMENTS

| | | | |
|---|---|---|---|
| 3,211,758 | 10/1965 | Tarkoey | 260/397.45 |
| 3,499,016 | 3/1970 | Lincoln et al. | 260/397.45 |
| 3,758,524 | 9/1973 | Anner et al. | 260/397.45 |
| 3,992,422 | 11/1976 | Green | 260/397.45 |
| 4,021,459 | 5/1977 | Green | 260/397.45 |
| 4,113,680 | 9/1978 | Kamano et al. | 260/397.45 |

FOREIGN PATENT DOCUMENTS 913941 12/1962 United Kingdom ........... 260/397.45

*Primary Examiner*—Elbert L. Roberts

*Attorney, Agent, or Firm*—Michael W. Glynn; Prabodh I. Almaula

[57] ABSTRACT

Novel halogenated steroids of the formula

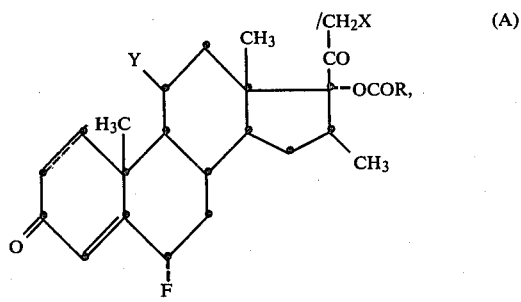

in which
X represents a halogen atom having a maximum atomic number of 17,
Y represents a hydrogen atom or hydroxyl, and
R represents an alkyl radical having a maximum of 6 carbon atoms, and their 1,2-dehydro derivatives and the processes for the production thereof.

36 Claims, No Drawings

HALOGENATED STEROIDS

The present invention relates to novel halogenated steroids of the formula

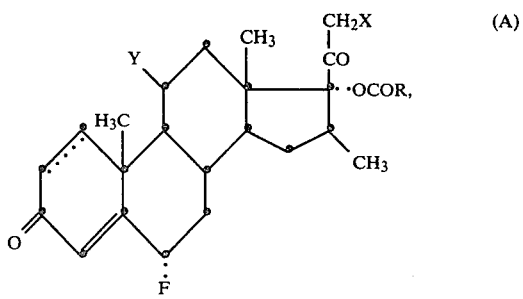

in which
X represents a halogen atom having a maximum atomic number of 17,
Y represents a hydrogen atom or hydroxyl, and
R represents an alkyl radical having a maximum of 6 carbon atoms,
the dotted line in the 1,2-position representing an additional double bond of a 1,2-dehydro derivative, pharmaceutical preparations containing these steroids and a novel process for the manufacture thereof.

The halogen characterised by the symbol X is fluorine or, preferably, chlorine.

The alkyl characterised by the symbol R may be branched, such as 2-propyl or 1,1-dimethylethyl, but is preferably a straight-chain alkyl, such as methyl, propyl, butyl, pentyl or hexyl and especially ethyl.

The manufacture of complicated polysubstituted compounds of this type from simple crude materials or intermediates in the industrial production of steroids necessitates a multi-stage method of synthesis in which each individual functional group is introduced separately, a group that has already been introduced often having to be protected temporarily later against undesired further conversion. The sequence of the individual synthesis steps, which are generally known per se from analogy processes is often of crucial importance for the economy of the entire synthesis. In the synthesis strategy, that is to say, in the selection of process variants and their sequence, special care is generally taken not to introduce sensitive functional groups until the later stages of synthesis in order to avoid any interference by the subsequent operations. Such sensitive groups undoubtedly include 21-fluoro and especially 21-chloro especially if its reactivity is further increased by an adjacent 20-oxo group. The usual synthesis strategy is therefore not to introduce these halogen atoms into the 21-position until the later stages, if not the last stage, of the synthesis. For the introduction itself, there are several, mainly indirect, methods available which are based on a common principle, viz. the exchange of a suitably esterified 21-hydroxyl group for the desired halogen, cf. U.S. Pat. No. 4,113,680 and U.S. Pat. No. 3,992,422, and the prior art indicated therein. For this method, however, the 21-hydroxyl group must for its part also be introduced beforehand, which, in normal cases, again necessitates several reaction stages; in addition, this group is itself so reactive that it must be protected during the synthesis, usually in the form of an ester. A classical synthesis strategy of this type can be demonstrated using as an example the synthesis of 6α,21-difluoro-11β,17α-dihydroxy-16α-methyl-pregna-1,4-diene-3,20-dione according to U.S. Pat. No. 3,499,016, in which no fewer than 10 process steps are required for the introduction of 3 functional groups (6α- and 21-fluoro, 17α-hydroxyl), an oxygen-containing functional group in the 21-position already being present from the beginning.

The process according to the invention is based on the unexpected discovery that 21-chloro-20-oxo steroids, and also their 21-fluoro analogues, have a considerably higher chemical stability than had generally been supposed. It has surprisingly now been found that the halogen atom remains intact under the normal conditions of various conventional conversions of industrial steroid synthesis and does not require special protective measures for its retention that go beyond the scope of normal production conditions.

A consequential application of these findings led to the development of the present process of the invention which, via novel intermediates and by a short, simple method, yields the compounds of the formula I, as illustrated by the reaction schemes I and II. In these schemes X and R have the meanings given above and Ac represents a lower alkanoyl radical having from 1 to 7 carbon atoms, for example one derived from the above-defined alkyl radical R, but especially an acetyl or formyl radical. (To distinguish therefrom, throughout the entire description the similar radical R.CO—, which, however, according to the definition given at the beginning has from 2 to 7 carbon atoms, will be termed the lower alkanecarbonyl radical).

The present invention also relates to the novel intermediates for the manufacture of the compounds of the formula A, namely 21-chloro-3β-hydroxy-16-methyl-pregna-5,16-dien-20-one and lower alkanoyl esters thereof, 21-chloro-3β-hydroxy-16β-methyl-5α,6;-16α,17-diepoxy-pregnan-20-one and the lower alkanoyl esters thereof, 21-chloro-6β-fluoro-3β,5α,17α-trihydroxy-16-methylene-pregnan-20-one and the 3-lower alkanoyl esters and 3-lower alkanoyl-5,17-di-lower alkanecarbonyl esters thereof, 21-chloro-6β-fluoro-3β,5α,17α-trihydroxy-16β-methyl-pregnan-20-one and the 5,17-di-lower alkanecarbonyl esters and 3-lower alkanoyl-5,17-di-lower alkanecarbonyl esters thereof, 21-chloro-6β-fluoro-5α,17α-di-lower alkanecarbonyloxy-16β-methyl-pregnane-3,20-dione, 21-chloro-6β-fluoro-17α-lower alkanecarbonyloxy-16β-methyl-pregn-4-ene-3,20-dione, and analogues of all the mentioned compounds in which 21-fluoro appears in place of 21-chloro. The invention also relates to the process for the manufacture of these compounds according to schemes I and II.

Of these, especially preferred compounds are: 21-chloro-3β-hydroxy-16-methyl-pregna-5,16-dien-20-one formate and acetate, 21-fluoro-3-hydroxy-16-methyl-pregna-5,16-dien-20-one and the 3-formate and 3-acetate thereof, 21-chloro-3-hydroxy-16β-methyl-5α,6;-16α,17-diepoxy-pregnan-20-one formate and acetate 21-fluoro-3β-hydroxy-16β-methyl-5α,6;16α,17-diepoxy-pregnan-20-one, the 3-formate and 3-acetate thereof, 21-chloro-6α-fluoro-3β,5α,17α-trihydroxy-16-methylene-pregnan-20-one 3-formate and 3-acetate, and also 3-formate 5,17-dipropionate and 3-acetate 5,17-dipropionate, 6β,21-difluoro-3β,5α,17α-trihydroxy-16-methylene-pregnan-20-one 3-formate and 3-acetate, and also 3-formate 5,17-dipropionate and 3-acetate, 5,17-dipropionate, 21-chloro-6β-fluoro-3β,5α,17α-trihydroxy-16β-methyl-pregnan-20-one 5,17-dipropionate, 3-formate 5,17-dipropionate and 3-acetate 5,17-dipropionate, 6β,21-difluoro-3β,5α,17α-trihydroxy-16β-methyl-pregnan-20-one 5,17-dipropionate, 3-formate 5,17-dipropionate and 3-acetate 5,17-dipropionate, 21-chloro-5α,17α-dihydroxy-16β-methyl-pregnan-3,20-dione 5,17-dipropionate, 6β,21-difluoro-5α,17α-dihydroxy-16β-methyl-pregnane-3,20-dione 5,17-dipropionate, 21-chloro-6α-fluoro-17α-hydroxy-16β-methyl-pregn-4-ene-3,20-dione 17-propionate, 6α,21-difluoro-17α-hydroxy-16β-methyl-pregn-4-ene-3,20-dione 17-propionate, 21-chloro-6α-fluoro-17α-hydroxy-16β-methyl-pregna-1,4-diene-3,20-dione 17-propionate, 6α,21-difluoro-17α-hydroxy-16β-methyl-pregna-1,4-diene-3,20-dione 17-propionate, 6α,21-difluoro-17α-hydroxy-16β-methyl-pregna-1,4-diene-3,20-dione 17-propionate, and also 21-chloro-6α-fluoro-11β,17α-dihydroxy-16β-methyl-pregn-4-ene-3,20-dione 17-propionate, 6α,21-difluoro-11β,17α-dihydroxy-16β-methyl-pregn-4-ene-3,20-dione 17-propionate, 21-chloro-6α-fluoro-11β,17α-dihydroxy-16β-methyl-pregna-1,4-diene-3,20-dione 17-propionate and 6α,21-difluoro-11β,17α-dihydroxy-16β-methylpregna-1,4-diene-3,20-dione 17 propionate.

The novel compounds of the formula A have valuable pharmacological properties, especially an outstanding anti-inflammatory activity, as shown when administered, for example locally, as a means of inhibiting the inflammatory processes. Thus, in Tonelli's dermatitis inhibition test on the ears of rats, the $ED_{50}$ (effective dose producing 50% inhibition of the experimental dermatitis) of 21-chloro-6α-fluoro-17α-hydroxy-16β-methyl-pregn-4-ene-3,20-dione 17-propionate was 53 μg/ml and the $ED_{50}$ of 21-chloro-6α-fluoro-11β,17α-dihydroxy-16β-methyl-pregn-4-ene-3,20-dione 17-propionate was 12 μg/ml. Due to this property, the compounds of the formula A can be used in all indications for which glucocorticoid steroids having anti-inflammatory properties are suitable but especially as anti-inflammatory glucocorticoids to be applied topically, for example for the treatment of inflammatory dermatoses, such as eczemas and dermatides, or partially corticoid-resistant dermatoses, for example psoriasis.

In addition, the compounds of the formula A are especially valuable intermediates for the manufacture of other useful substances, especially other pharmacologically active steroids. In this connection they have, for example, a key position in the synthesis of highly anti-inflammatorily active, topically administrable corticosteroids, such as 21-chloro-6α-fluoro-9α-halo-11β-hydroxy-16β-methyl-17α-propionyloxy-pregna-1,4-diene-3,20-dione and analogues thereof according to British Pat. No. 1,563,638. For conversion into these valuable therapeutic agents, all that may be necessary in the case of a compound of the formula A is the straightforward conventional introduction of 9-chloro or 9-fluoro.

The novel compounds mentioned are manufactured according to the invention by, in succession, (a) introducing the halogen X into the 21-position of 3β-hydroxy-16-methyl-pregna-5,16-dien-20-one or a carboxylic acid ester, such as, especially, a 3-lower alkanoyl ester, thereof, (b) esterifying the resulting 21-X-3β-hydroxy-16-methyl-pregna-5,16-dien-20-one to form a 3-lower alkanoyl ester and simultaneously epoxidising with a peracid in the 5,6- and 16,17-positions, (c) in a resulting 5,6;16,17-diepoxide, rearranging the 16α,17α-epoxide ring by catalysis with a strong acid to form the 16-methylene-17α-hydroxy grouping, convertig the 5α,6α-epoxide ring using hydrogen fluoride into the 6β-fluoro-5α-hydroxy grouping and esterifying the 5- and 17-hydroxyl groups, (d) catalytically hydrogenating the resulting 21-X-6β-fluoro-3β,5α,17α-trihydroxy-16-methylene-pregnan-20-one 3-lower alkanoyl-5,17-di-lower alkanecarbonyl ester, (e) in the resulting corresponding 16β-methyl compound, freeing the esterified 3-hydroxyl group by selective hydrolysis and converting it into the 3-oxo group by treatment with an oxidising agent, (f) in a resulting 21-X-6β-fluoro-5α,17α-di-lower alkanecarbonyloxy-16β-methyl-pregnane-3,20-dione, removing the 5-positioned lower alkanecarbonyloxy group by means of acid and converting the 6β-fluoro by catalysis with a strong acid into the 6α-fluoro isomer, and, if a product of the formula A is desired in which Y represents hydroxyl, hydroxylating in the 11β-position a resulting end product in which Y represents hydrogen by means of the enzymatic system of a 11β-hydroxylating micro-organism, and/or, if a 1,2-dehydro compound of the formula A is desired, dehydrogenating a resulting 1,2-saturated end product of the formula A. Although all the individual process operations are carried out in a conventional manner known per se, there are other unexpectedly favourable results in some stages which are obviously connected with the special structure of the novel compounds.

For the first stage of synthesis (called stage A in scheme I) of the process according to the invention, that is to say, for the introduction of the 21-positioned halogen atom X, there are several general processes available and for this purpose a reactive ester of the corresponding 21-hydroxy compound, especially the 21-iodide or -sulphonate, such as 21-mesylate, is reacted with a lithium or silver salt of the desired halogen in a polar solvent. The introduction of the halogen X is, however, carried out especially according to the general process of U.S. Pat. No. 3,758,524 by converting the known starting material of the formula I under the catalytic effect of an alkali metal lower alcoholate, for example sodium ethoxide, sodium methoxide or potassium tert.-butoxide, with a lower alkyl oxalate or formate, for example dimethyl oxalate, diethyl oxalate or ethyl formate, into the corresponding 21-lower alkoxalyl derivative, for example the methoxalyl or ethoxalyl derivative, (formula II, X=—CO.CO.O.lower alkyl) or 21-formyl derivative (formula II, X=—CH=O), forming from this by treatment with an organic sulphonylazide, for example p-tosylazide, the novel 21-diazo-3β-hydroxy-16-methyl-pregna-5,16-dien-20-one and treating this with hydrogen fluoride, or in an analogous manner with hydrogen chloride, to form the corresponding 21-halo compound of the formula II.

This compound is then esterified in a manner known per se to form the corresponding 3β-lower alkanoyl ester of the formula III. If the corresponding 3-formate (formula III, Ac=HC(=O)—) is desired, then advantageously excess formic acid may be used for esterification, preferably an approximately 85% aqueous formic acid, which is used simultaneously as a solvent, and the operation may be carried out at an elevated temperature of up to approximately 100° C. In the case of other lower alkanoyl esters, for example the acetate, the 3- hydroxy compound of the formula II is treated in the usual manner with a reactive derivative of the corresponding lower alkanoic acid, such as a chloride or a different mixed anhydride, for example one with trifluoroacetic acid, or especially the symmetrical anhydride, for example with acetic anhydride, in the presence of at least one molar equivalent of a tertiary organic base and optionally in an aprotic organic solvent in the temperature range of from approximately −10° to approximately 30°, generally at room temperature. Preferably, an organic base of this type is used that is incapable, for example as a result of steric hindrance, of forming a quaternary salt with the 21-halide; preferably used as such a base is, for example, a 2,6-disubstituted, especially dialkylated, pyridine derivative, for example 2,4,6-collidine or especially 2,6-lutidine.

The next stage (called B in scheme I) of the process according to the invention is the epoxidation of the 5,16-diene of the formula III with an organic peracid (peroxy acid) or an analogous known epoxidising agent. The reaction is carried out in the conventional manner at temperatures of from approximately −15° to approximately +30°, especially between approximately 0° and room temperature, in an inert organic solvent, especially an ether, such as diethyl ether, 1,2-dimethoxyethane or tetrahydrofuran, or a halogenated hydrocarbon, such as chloroform or methylene chloride, preferably in the absence of water. The epoxidising agent used is especially an optionally substituted peroxybenzoic acid, such as perbenzoic acid, monoperphthalic acid ("perphthalic acid") or especially m-chloroperbenzoic acid. The reactant acts on two positions of the molecule simultaneously: while the epoxidation of the 16,17-double bond takes place with a high stereospecificity and results practically exclusively in the 16α,17α-epoxide ring, the epoxidising agent attacks the 5,6-double bond from both sides; consequently, in addition to the 5α,6;-16α,17-diepoxide of the formula IVa formed as the main product, the epimeric 5β,6;16α,17-diepoxide of the formula IVb is formed as a by-product in the ratio of approximately 4:1. The epimers are readily separated by the usual physical methods, such as crystallisation and/or chromatography, and are also processed separately in the next stage.

The next stage (called C in scheme I) of the process according to the invention comprises the acidically catalysed rearrangement of the 16α,17-epoxide ring into the 16-methylene-17α-hydroxy grouping and the conversion of the 5α,6-epoxide ring into the 6β-fluoro-5α-hydroxy grouping. It is especially advantageous to carry out both conversions in a single operation by treating the corresponding 5α,6;16α,17-diepoxide of the formula IVa with hydrogen fluoride which not only possesses the fluoride anion necessary for the 6β-fluorination but also, at the same time, the acidity necessary for the rearrangement of the 16,17-epoxide. The reaction can be carried out with approximately 40% aqueous, or preferably with anhydrous liquid, hydrogen fluoride, for example under conditions such as are customarily used in the conventional conversion of a 9β,11-epoxide into the corresponding 9α-fluoro-11β-hydroxy compound. The operation is advantageously carried out in excess HF as solvent, and optionally also in the presence of an inert solvent, such as chloroform, tetrahydrofuran, dioxan, or especially dimethylformamide. Hydrogen fluoride may also be used in the form of a hydrogen fluoride-yielding agent, for example a salt with a tertiary organic base, or especially a similar addition compound, for example an adduct with a carbamic or thiocarbamic acid derivative, especially as an adduct with urea according to U.S. Pat. No. 3,211,758. Surprisingly, this reaction yields as the only isomer the 16-methylene-17α-hydroxy compound of the formula V, the formation of the $\Delta^{15}$-16-methyl-17α-hydroxy-isomer, which is often produced as the main product in the rearrangement of a 16β-methyl-16α,17α-epoxide by means of hydrogen fluoride, not being detected in the present case.

Several intermediate stages are required for the conversion according to the invention of an epimeric 5β,6;16α,17-diepoxide of the formula IVb into the fluorohydrine of the formula V since the unfavourable β-configuration of the 5,6-epoxide ring must first be converted into the desired α-configuration. The multi-stage conversion is carried out according to scheme II by reacting the corresponding 5β,6;16α,17-diepoxide of the formula IVb with a strong oxygen-containing acid, treating the resulting 5α,6β,17α-trihydroxy-16-methylene compound of the formula XI with methanesulphonyl chloride or a similar organic sulphonyl halide in the presence of an organic base and reacting the resulting 5α,6-epoxy-17α-hydroxy-16-methylene compound XII, which has the correct α-configuration of the epoxide ring, with hydrogen fluoride and so converting into the fluorohydrine of the formula V. The reaction with a strong acid (stage $C_a'$ in scheme II) is carried out in the conventional manner, for example in the presence of small quantities of water in an organic solvent, such as a lower alkanol, for example methanol or ethanol, an ether, for example diethyl ether, or especially tetrahydrofuran or dioxan, or a halogenated hydrocarbon, for example chloroform, or in a mixture thereof; the acid used is an inorganic acid, such as perchloric acid or especially sulphuric acid, or an organic sulphonic acid, such as especially p-toluenesulphonic acid. The reaction may be carried out with catalytic quantities of the acid in a wide temperature range up to the boiling point of the reaction mixture, but the operation is preferably carried out under mild conditions at room temperature. For the second stage ($C_b'$ in scheme II), i.e. the treatment with a sulphonyl halide, conditions are applied that are analogous to those described above for the base-catalysed esterification of the 3-hydroxyl group, with special care being given to the choice of a suitable base. The third stage (called $C_c'$ in scheme II), that is to say, the splitting of the 5α,6α-epoxide ring in the compound of the formula XII to form the corresponding fluorohydrine of the formula V, is carried out in the same manner as described in detail above for the treatment of the diepoxide IVa with hydrogen fluoride. The entire three-stage process is advantageous especially for carrying out the process according to the invention on an industrial scale as a contingent measure for utilising the by-product of the formula IVb and for the additional increase in the total yield of the intermediate of the formula V.

Following the splitting of the diepoxides IVa and IVb, the two free hydroxyl groups in the resulting 21-X-6β-fluoro-5α,17α-dihydroxy 3β-lower alkanoyloxy-16-methylene-pregnan-20-one are esterified by the above-defined radical —COR of a lower alkanecarboxylic acid to form the corresponding 3,5,17-triester of the formula VI. For this purpose, conventional methods are used that are known per se for the esterification of tertiary hydroxyl groups that are difficult to esterify, for example the treatment of the compound of the formula V, which has such a hydroxyl group in the 5α-position and in the 17α-position, with a symmetrical anhydride of a suitable lower alkanecarboxylic acid, for example with propionic acid anhydride, with catalysis by means of a strong mineral acid, such as, especially, perchloric acid, or an organic sulphonic acid, such as p-toluenesulphonic acid. The esterifying agent especially used is, however, a reactive mixed anhydride of the corresponding lower alkanecarboxylic acid, especially one with trifluoroacetic acid, for example the mixed propionic acid/trifluoroacetic acid anhydride. The reaction usually takes place at room temperature with the exclusion of water in an inert organic solvent, such as an optionally halogenated hydrocarbon, for example benzene, toluene or cyclohexane, or chloroform or methylene chloride, or an ether, such as diethyl ether, dioxan or tetrahydrofuran, with excess esterifying agent. This agent is advantageously prepared in the reaction mixture immediately before the reaction by mixing the corresponding lower alkanecarboxylic acid with an approximately equivalent quantity of trifluoroacetic anhydride, optionally while cooling, and allowing the reaction to take place for 30–60 minutes at room temperature.

The next stage (called stage D in scheme I) of the process according to the invention is the catalytic hydrogenation of a 16-methylene derivative of the formula VI to form the corresponding 16β-methyl compound of the formula VII. The hydrogenation is carried out in the conventional manner, for example with elementary hydrogen at atmospheric or slightly elevated pressure (up to approximately 5 atmospheres) at temperatures in the region of room temperature in the usual organic solvents, such as ethers, for example 1,2-dimethoxyethane, dioxan or tetrahydrofuran, lower alkanols, for example methanol or ethanol, or lower aliphatic esters, for example ethyl acetate. The catalyst used may be the usual finely divided metal catalysts, such as the Raney metals, especially Raney nickel, or noble metals, for example rhodium or, very especially, platinum, which may also be finely divided on a suitable carrier, such as silica gel or aluminium oxide. As the only special measure during hydrogenation, care must be taken that the 21-positioned halogen atom is not removed by reduction: too energetic conditions, such as elevated temperature and agents having a basic reaction, should especially be avoided. It is extremely surprising that this hydrogenation yields practically exclusively the 16β-methyl epimer, although in the known analogous cases considerable quantities of the 16α-methyl epimer are formed at the same time.

In the next stage (called stage E in scheme I) of the process according to the invention, the esterified 3β-hydroxyl group in the 21-X-6β-fluoro-3β,5α,17α-trihydroxy-16β-methyl-pregnan-20-one 3-lower alkanoyl-5,17-di-lower alkanecarbonyl ester of the formula VII is first freed hydrolytically (whereby the 5,17-di-lower alkanecarbonyl ester of the formula VIII is formed) and is then oxidised to form the 3-oxo group. The selective hydrolytic liberation of the secondary 3β-hydroxyl group in the presence of analogously esterified tertiary hydroxyl groups in the 5α- and 17α-positions is carried out in a manner known per se by acid catalysis, for example in a lower alkanol, such as methanol, ethanol or isopropyl alcohol, in the presence of a mineral acid, such as hydrochloric acid or sulphuric acid. If the 3-hydroxyl group in the starting material of the formula VII is in the form of a formate, the selective liberation is especially easy and can even be effected with weakly basic agents, for example with one equivalent of an alkali metal bicarbonate, such as sodium or potassium bicarbonate, at room temperature. The subsequent oxidation (dehydrogenation) of the free 3β-hydroxyl group to form the oxo group, with the formation of the 21-X-6β-fluoro-5α,17α-di-lower alkanecarboxyloxy-16β-methyl-pregnane-3,20-dione of the formula IX, is also carried out in the conventional, generally known manner, for example with a compound of hexavalent chromium, such as chromium trioxide or chromic acid and its alkali metal salts, a lower alkanecarboxylic acid, such as acetic acid or propionic acid, or a ketone, such as acetone, being used as the reaction medium, optionally diluted by a halogenated lower alkane, such as dichloromethane or chloroform, and the reaction temperature preferably being maintained below room temperature. A preferred variant is oxidation with a solution of chromium trioxide in aqueous sulphuric acid (Jones reagent), which is generally carried out in acetone at a temperature of between approximately −10° and approximately 25°, preferably in the region 0°.

The next stage (called stage F in scheme I) of the process according to the invention consists in the acidic β-elimination of the esterified 5α-hydroxyl group of the 3-ketone of the formula IX with the formation of the 4,5-double bond conjugated with the oxo group, and in the acidically catalysed isomerisation of the 6β-positioned fluorine atom to form the thermodynamically more stable 6α-configuration, whereby the 21-X-6α-fluoro-17α-lower alkanecarbonyloxy-16β-methyl-pregn-4-ene-3,20-dione of the formula X is formed. The slight acidity of a carboxylic acid is sufficient for the β-elimination of the 5-positioned lower alkanecarbonyloxy group; in a manner known per se, liquid carboxylic acids, which at the same time serve as solvents, are especially suitable for this purpose, especially lower aliphatic monocarboxylic acids, such as, above all, glacial acetic acid. The operation is preferably carried out at an elevated temperature of from approximately 50° to the boiling temperature of the reaction mixture. The acidity of the acids mentioned is, however, generally insufficient for the complete isomerisation of the 6-positioned fluorine atom; in that case it is necessary to subject the product of the elimination described above to an additional isomerisation process with a stronger acid. Since strong acids do not have a detrimental effect on β-elimination when used carefully, the two conversions may be advantageously combined in a single operation by treating the compound of the formula IX in a manner known per se with a catalytic quantity of a strong acid in an inert organic solvent. The acid used is either an inorganic acid, for example sulphuric acid, perchloric acid or a hydrohalic acid, such as, especially, hydrochloric acid or hydrobromic acid, or a strong organic acid, for example a sulphonic acid, such as, especially, p-toluenesulphonic acid. Suitable solvents are, for example, especially the above-mentioned liquid carboxylic acids, especially glacial acetic acid, and halogenated hydrocarbons, such as chloroform and methylene chloride, and mixtures thereof. The reaction temperature is generally between zero and room temperature. The reaction is especially carried out in a chloroform solution with gaseous dry hydrogen chloride at approximately 0°.

The resulting 1,2-saturated 11-unsubstituted end products of the process according to the invention described above which are characterised by the formula A in which Y represents hydrogen and in which there is a single bond in the 1,2-position, may then, if desired, be modified by additional structural features by introducing the 11β-hydroxyl group and/or the 1,2-double bond in any sequence.

For the purpose of the optional introduction of the 11β-hydroxyl group, according to stage G in scheme I of the process according to the invention the 21-X-6α-fluoro-17α-lower alkanecarbonyloxy-16β-methyl-pregn-4-ene-3,20-dione or -1,4-diene-3,20-dione of the formula Aa is subjected to a biological 11β-hydroxylation to form the 21-X-6α-fluoro-11β-hydroxy-17α-lower alkanecarbonyloxy-16β-methyl-pregn-4-ene-3,20-dione or -1,4-diene-3,20-dione (21-X-6α-fluoro-11β,17α-dihydroxy-16β-methyl-pregn-4-ene-3,20-dione 17-lower alkanecarbonyl ester or its 1,2-dehydro analogues) of the formula Ab. The hydroxylation is carried out according to the methods of biological transformation known per se that are generally used for the introduction of the 11β-hydroxyl group in steroids of the pregnane series, and takes place by means of the corresponding enzyme system of a known 11β-hydroxylating micro-organism, such as *Aspergillus niger, Cunninghamella blakesleana* or especially *Curvularia lunata*. In the present case, this 11β-hydroxylation has a considerable unexpected advantage: the esterified 17α-hydroxyl group is not freed during transformation as is generally the case in such microbiological processes but is retained intact. In the case of this transformation, the hydroxylating enzyme system may be located directly in the cell of a living micro-organism and acts, in one variant of the hydroxylating process, during the cultivation of the micro-organism in an appropriate conventional nutrient medium or, in another variant, in a static culture which is prepared, for example, by separating mechanically the cultivated micro-organism from the nutrient solution and suspending in a nutrient-free aqueous medium. As is known, however, it is also possible to use a hydroxylating enzyme system in a cell-free form, for example a product obtained by carefully killing and/or destroying the cell wall of the micro-organism, or to use a more or less enriched or purified enzyme preparation. The hydroxylated steroid of the formula A is isolated from the substrate in a conventional manner, generally by extraction with suitable organic solvents, for example halogenated hydrocarbons or lower aliphatic esters, such as chloroform, methylene chloride or ethyl acetate.

The optional subsequent introduction of the 1,2-double bond into the 1,2-saturated compounds to form corresponding 1,2-dehydro derivatives is carried out in a manner known per se, for example by dehydrogenation. Biological dehydrogenation processes may be used for this purpose, for example dehydrogenation by means of the micro-organisms *Corynebacterium simplex* or *Septomyxa affinis* or their enzyme systems, or treament with selenium dioxide in an organic solvent, for example tert.-butyl alcohol. Preferably, however, 2,3-dichloro-5,6-dicyano-1,4-benzoquinone is allowed to act at approximately boiling temperature for several hours, for example 6–24 hours; a conventional solvent is used, for example an aromatic hydrocarbon, such as benzene or xylene, a lower aliphatic alcohol, such as ethanol, propanol or tert.-butyl alcohol, a lower aliphatic ketone, such as acetone or 2-butanone, an aliphatic ester, such as ethyl acetate, or a cyclic ether, such as dioxan or tetrahydrofuran.

The reactants and intermediates used in the process according to the invention described above are preferably those that yield the end products and intermediates that have been given special mention, especially the end products and intermediates that have been specifically named.

Throughout the whole description, unless specifically defined, the term "lower" in connection with a hydrocarbon radical refers to one having a maximum of 7 carbon atoms.

The invention also relates to those embodiments of the above process in which a compound obtainable as an intermediate at any stage is used as the starting material and the remaining steps are carried out or in which a starting material is formed under the reaction conditions.

The present invention also relates to pharmaceutical preparations, for humans and mammals, that contain the above-described novel compounds of the formula A in a therapeutically active quantity as active substances together with a pharmaceutical carrier, and also to the manufacture thereof. There are used as carriers organic or inorganic substances that are suitable for enteral, especially oral, and intrauterine, parenteral or topical administration. Suitable for the formation of these carriers are substances that do not react with the novel compounds, such as, for example, water, gelatin, lactose, starch, magnesium stearate, talc, vegetable oils, benzyl alcohol, gums, polyalkylene glycols, petroleum jelly, cholesterol and other known medicament carriers. The pharmaceutical preparations may be in solid form, for example in the form of tablets, dragées or capsules, or in liquid or semi-liquid form as solutions, suspensions, emulsions, ointments or creams. Optionally, these pharmaceutical preparations are sterilised and/or contain adjuncts, such as preservatives, stabilisers, wetting agents, emulsifiers, salts for altering the osmotic pressure, or buffers. They may also contain other therapeutically valuable or biologically active substances.

Especially suitable are topically administrable pharmaceutical preparations, such as creams, ointments, pastes, foams, tinctures and solutions, that contain from approximately 0.01% to approximately 0.5% of the active substance.

Creams are oil-in-water emulsions that contain more than 50% of water. Substances used as the oily base are especially fatty alcohols, for example lauryl alcohol, cetyl alcohol or stearyl alcohol, fatty acids, for example palmitic acid or stearic acid, liquid to solid waxes, for example isopropyl myristate, wool wax or beeswax, and/or hydrocarbons, for example petroleum jelly (Petrolatum) or paraffin oil. Emulsifiers that can be used are surface-active substances that have predominantly hydrophilic properties, such as corresponding non-ionic emulsifiers, for example fatty acid esters of polyalcohols or ethylene oxide adducts thereof, such as polyglycerol fatty acid esters or polyoxyethylene sorbitan fatty acid esters (Tweens) and also polyoxyethylene fatty alcohol ethers or polyoxyethylene fatty acid esters, or corresponding ionic emulsifiers, such as alkali metal salts of fatty alcohol sulphates, for example sodium lauryl sulphate, sodium cetyl sulphate or sodium stearyl sulphate, which are customarily used in the presence of fatty alcohols, for example cetyl alcohol or stearyl alcohol. Additives to the aqueous phase are, inter alia, agents that reduce the drying out of the creams, for example polyalcohols, such as glycerol, sorbitol, propylene glycol and/or polyethylene glycols, and also preservatives and perfumes.

Ointments are water-in-oil emulsions that contain up to 70%, but preferably from approximately 20% to approximately 50%, of water or of an aqueous phase. Substances that can be used as the fatty phase are especially hydrocarbons, for example petroleum jelly, paraffin oil and/or hard paraffins, which, in order to improve the water-binding capacity, preferably contain suitable hydroxy compounds, such as fatty alcohols or esters thereof, for example cetyl alcohol or wool wax alcohols, or wool wax. Emulsifiers are corresponding lipophilic substances, such as sorbitan fatty acid esters (Spans), for example sorbitan oleate and/or sorbitan isostearate. Additives to the aqueous phase are, inter alia, humectants, such as poly-alcohols, for example glycerol, propylene glycol, sorbitol and/or polyethylene glycol, and also preservatives and perfumes.

Fatty ointments are anhydrous and contain, as the base, especially hydrocarbons, for example paraffin, petroleum jelly and/or liquid paraffins, and also natural or partially synthetic fats, for example coconut fatty acid triglyceride, or preferably hardened oils, for example hydrogenated groundnut oil or castor oil, and also fatty acid partial esters of glycerol, for example glycerol monostearate and glycerol distearate, as well as, for example, the fatty alcohols, which increase the water absorption capacity, and emulsifiers and/or additives mentioned in connection with the ointments.

Pastes are creams and ointments containing secretion-absorbing powder constituents, such as metal oxides, for example titanium oxide or zinc oxide, and also talc and/or aluminium silicates, the task of these constituents being to bind any moisture or secretions.

Foams are administered from pressurized containers and are liquid oil-in-water emulsions in an aerosol form and the propellants used are halogenated hydrocarbons, such as chlorofluoro-lower alkanes, for example dichlorodifluoromethane and dichlorotetrafluoroethane. Substances used as the oily phase are, inter alia, hydrocarbons, for example paraffin oil, fatty alcohols, for example cetyl alcohol, fatty acid esters, for example isopropyl myristate, and/or other waxes. The emulsifiers used are, inter alia, mixtures of those having predominantly hydrophilic properties, such as polyoxyethylene sorbitan fatty acid esters (Tweens), and mixtures of those having predominantly lipophilic properties, such as sorbitan fatty acid esters (Spans). The customary additives, such as preservatives, are also used.

Tinctures and solutions usually have an aqueous-ethanolic base to which are added, inter alia, polyalcohols, for example glycerol, glycols and/or polyethylene glycol, as humectants in order to reduce evaporation, fat-restoring substances, such as fatty acid esters with low polyethylene glycols, that is to say lipophilic substances soluble in the aqueous mixture, to replace the fatty substances withdrawn from the skin by the ethanol, and, if necessary, other adjuncts and additives.

The topically administrable pharmaceutical preparations are manufactured in a manner known per se, for example by dissolving or suspending the active substance in the base or, if necessary, in a part thereof. When the active substance is processed as a solution, it is as a rule dissolved in one of the two phases before emulsifying; when it is processed as a suspension, it is mixed with part of the base after emulsifying and then added to the rest of the formulation.

The dosage of the active substance, for example the compounds given special mention above, is in principle analogous to that of recognised topical anti-inflammatory agents of the corticoid type; it depends, however, on the one hand on the species, body weight, age and individual condition of the warm-blooded animal and on the other on the method of administration and can be established in a routine test in known manner for each individual case.

The invention also relates to a method of alleviating or eliminating pathological inflammatory conditions of the body, and especially the skin, of a warm-blooded animal, especially humans, which method is characterised by the treatment of this body or part of the body, preferably by topical administration, with an anti-inflammatorily active quantity of a compound of the formula A, alone or in the form of a pharmaceutical preparation. The term "an anti-inflammatorily active quantity" should be understood as meaning a quantity of the active substance sufficient for a significant inhibition of the inflammation.

In the following Examples, the implementation of the present invention is illustrated in more detail without thereby limiting its scope. The temperatures given hereinbefore and hereinafter are in degrees Centigrade.

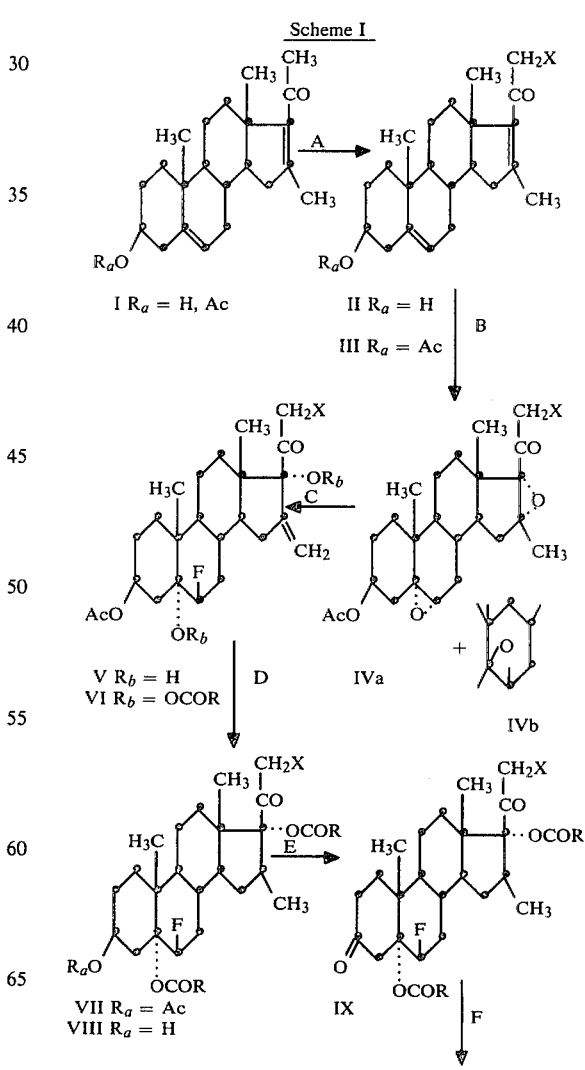

Scheme I

-continued
Scheme I

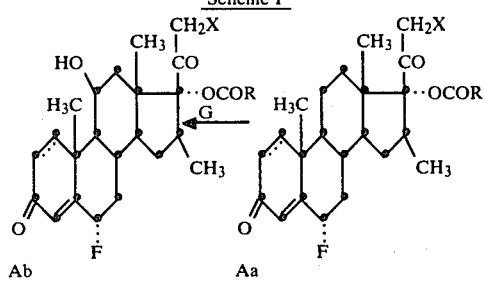

Scheme II

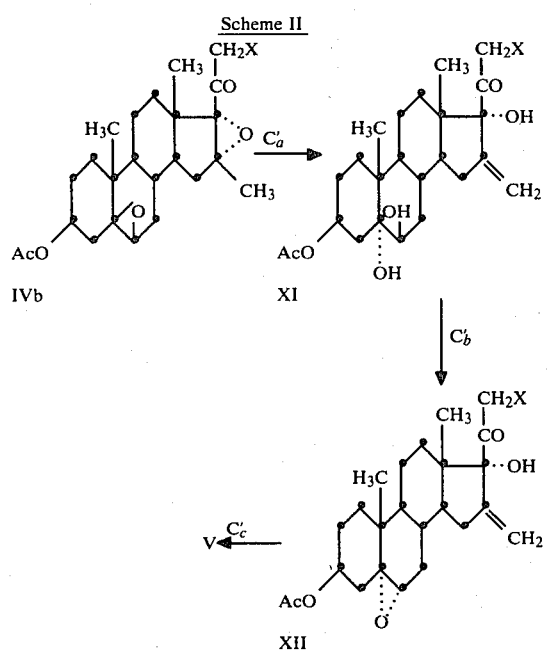

EXAMPLE 1

94.3 g of pulverulent sodium methoxide are added under a nitrogen stream and while cooling with ice to 943 ml of a stirred solution prepared by diluting 200 g of oxalic acid dimethyl ester with toluene to a total volume of 1 liter; the mixture is then rinsed with 900 ml of toluene, 117.6 g of crystalline 3β-hydroxy-16-methyl-pregna-5,16-dien-3-one acetate are added and rinsing is effected with another 900 ml of toluene and the whole is stirred for seven hours at room temperature. While cooling with ice, 64 ml of glacial acetic acid, 136.5 ml of triethylamine and 194.2 g of p-toluenesulphonylazide are added in succession to the mixture and then rinsing is effected with 585 ml of toluene; the cooling means is removed and the mixture is left to stand for 18 hours at room temperature. The reaction mixture is emptied onto semi-saturated sodium chloride solution, the organic layer is separated off and the aqueous layer is extracted again with chloroform; combined organic solutions are then washed with semi-saturated sodium chloride solution, dried and concentrated by evaporation in vacuo. The yellow crystalline residue is stirred for three hours with 5.8 l of tert.-butyl alcohol and 1.17 l of 2 N potassium hydroxide solution, emptied onto a semi-saturated sodium chloride solution and worked up as indicated above. The residue is dissolved in methylene chloride and filtered through 560 g of aluminium oxide (activity II). The eluates, washed out with 10 l of methylene chloride and 30 l of a mixture (v/v) of toluene/ethyl acetate (4:1), are concentrated by evaporation in vacuo. By recrystallising the residue from methylene chloride/ether, 103 g of 21-diazo-3β-hydroxy-16-methyl-pregna-5,16-dien-20-one having a melting point of 137°-139° (decomposition) are obtained.

EXAMPLE 2

3.42 l of a 3 N solution of hydrogen chloride in ether are added while stirring at −10° in a nitrogen stream to a mixture of 103 g of 21-diazo-3β-hydroxy-16-methyl-pregna-5,16-dien-20-one, 1.73 l of methylene chloride and 1.73 l of ether, and in so doing the temperature may rise to approximately 2°. After 15 minutes the cooling bath is removed, the mixture is emptied onto a solution of 1 kg of sodium acetate in 5 l of water, taken up in methylene chloride, washed with saturated sodium bicarbonate solution, dried and concentrated by evaporation in vacuo. By crystallising the residue from methanol, 87.65 g of 21-chloro-3β-hydroxy-16-methyl-pregna-5,16-dien-20-one having a melting point of 170°-172° are obtained.

EXAMPLE 3

A mixture of 86 g of 21-chloro-3β-hydroxy-16-methyl-pregna-5,16-dien-20-one, 800 ml of acetic anhydride and 172 ml of 2,6-lutidine is stirred for 137 hours in the dark at room temperature, poured onto 4 kg of ice and 7.2 l of water and stirred for a further two hours. The precipitate is filtered with suction, washed with water, dissolved in methylene chloride, dried and concentrated by evaporation in vacuo. The residue is filtered in a toluene solution through 430 g of silica gel and is extracted by washing with 18 l of toluene. The residue (90 g) obtained after concentrating the eluates by evaporation in vacuo can be processed directly in the next stage. After recrystallising a sample from methylene chloride/ether/pentane, the purified 21-chloro-3β-hydroxy-16-methyl-pregna-5,16-dien-20-one acetate melts at 183°-186°.

EXAMPLE 4

126 g of m-chloroperbenzoic acid are added while stirring and cooling with ice water to 91.45 g of crude 21-chloro-3β-hydroxy-16-methyl-pregna-5,16-dien-20-one acetate and 1.26 l of methylene chloride. After stirring for 18 hours at room temperature, the mixture is poured onto 3 l of saturated sodium bicarbonate solution, taken up in methylene chloride by extracting several times, washed in succession with 2.5 l of 1 N sodium thiosulphate solution and saturated sodium bicarbonate solution, dried and concentrated by evaporation in vacuo. The residue is chromatographed on 920 g of silica gel. The first fractions, eluted with a total of 7.5 l of toluene, are discarded and the following fractions are concentrated by evaporation in vacuo. The resulting residues are combined and recrystallised from methylene chloride/ether; the resulting 70.36 g of 21-chloro-5α,6;16α,17-diepoxy-3β-hydroxy-16β-methyl-pregnan-20-one acetate are contaminated with only a very small amount of the corresponding 5β,6-epoxide and are further processed in this degree of purity. A sample melts, after chromatographical purification, at 212°-214°.

After crystallisation from methylene chloride/ether, there are obtained from the mother liquor of the 5α,6- epoxide, 18.6 g of 21-chloro-5β,6;16α,17-diepoxy-3β-hydroxy-16β-methyl-pregnan-20-one acetate to which only small quantities of the corresponding 5α,6-epoxide adhere and which are further processed in this degree of purity. After recrystallising several times from methylene chloride/ether, a sample melts at 158°–160°.

EXAMPLE 5

1.3 l of a mixture of 1.8 l of dioxan and 54 ml of concentrated sulphuric acid are added to 13 g of 21-chloro-5β,6;16α,17-diepoxy-3β-hydroxy-16β-methyl-pregnan-20-one acetate. After six hours, the mixture is poured onto saturated sodium bicarbonate solution and extracted several times with a mixture (v/v) of chloroform/alcohol (7:3). The organic extracts are washed with saturated sodium chloride solution, dried and concentrated by evaporation in vacuo. 13.15 g of crude 21-chloro-3β,5α,6β,17α-tetrahydroxy-16-methylene-pregnan-20-one 3-acetate are obtained in the form of a foam. This foam is dissolved in 167 ml of 2,6-lutidine; 6.13 ml of methanesulphonyl chloride are added while stirring and cooling with ice and the mixture is stirred for 144 hours at 0°–5°. Ice is added to the mixture and stirring is effected for a further hour; the mixture is acidified with 300 ml of glacial acetic acid, taken up in several portions of methylene chloride, washed with saturated sodium bicarbonate solution, dried and concentrated by evaporation in vacuo. The residue is chromatographed on 260 g of silica gel and 21-chloro-5α,6-epoxy-3β,17α-dihydroxy-16-methylene-pregnan-20-one 3-acetate (5.2 g) having a melting point of 232°–234° is eluted with mixtures (v/v) of toluene/ethyl acetate (97:3) and (95:5).

EXAMPLE 6

A mixture of 7.5 g of 21-chloro-5α,6-epoxy-3β,17α-dihydroxy-16-methylene-pregnan-20-one 3-acetate in 150 ml of a previously prepared mixture of 56 parts by weight of hydrogen fluoride and 44 parts by weight of urea is stirred for 90 minutes at room temperature, poured onto 2.25 kg of ice and 1.13 l of concentrated aqueous ammonia solution and extracted several times with chloroform. The organic solutions are washed with semi-saturated sodium chloride solution, dried and concentrated by evaporation in vacuo. The residue is filtered in a chloroform solution through 150 g of silica gel, washed with 2 l of a mixture (v/v) of chloroform/ethyl acetate (9:1) and concentrated by evaporation. After recrystallising from methylene chloride/ether, 6.28 g of 21-chloro-6β-fluoro-3β,5α,17α-trihydroxy-16-methylene-pregnan-20-one 3-acetate having a melting point of 250°–253° (decomposition) are obtained.

1.93 g of the end product described above are obtained in an analogous manner from 5 g of 21-chloro-5α,6;16α,17-diepoxy-3β-hydroxy-16β-methyl-pregnan-20-one acetate and 100 ml of the above-defined hydrogen fluoride/urea mixture after the above-described processing and chromatography on 213 g of silica gel [elution with a mixture of toluene/ethyl acetate (9:1)].

EXAMPLE 7

A mixture, prepared 45 minutes beforehand, of 96 ml of propionic acid and 80 ml of trifluoroacetic anhydride is added while stirring to a mixture of 6.2 g of 21-chloro-6β-fluoro-3β,5α,17α-trihydroxy-16-methylene-pregnan-20-one 3-acetate and 40 ml of chloroform and the solution formed is left to stand for 17 hours in the dark at room temperature. The dark red-brown reaction solution is emptied onto ice and 200 g of sodium bicarbonate are added in the course of 45 minutes while stirring. After a further 30 minutes the product is taken up in methylene chloride, washed with saturated sodium bicarbonate solution, dried and concentrated by evaporation in vacuo. The residue in toluene solution is filtered through 160 g of silica gel and eluted with 6 l of a mixture (v/v) of toluene/ethyl acetate (4:1). The residue of the eluates concentrated by evaporation in vacuo is recrystallised from ether/pentane to yield 6.8 g of 21-chloro-6β-fluoro-3β,5α,17α-trihydroxy-16-methylene-pregnan-20-one 3-acetate, 5,17-dipropionate, melting point 171°–172°.

EXAMPLE 8

285 mg of 21-chloro-6β-fluoro-3β,5α,17α-trihydroxy-16-methylene-pregnan-20-one 3-acetate 5,17-dipropionate, 20 mg of platinum oxide and 25 ml of fine spirit are stirred in a hydrogen atmosphere at room temperature and under an overpressure of 100–200 torr until the absorption of hydrogen ceases. The catalyst is filtered with suction and then washed with methylene chloride and the filtrate is concentrated by evaporation in vacuo. After recrystallising the residue from alcohol, 21-chloro-6β-fluoro-3β,5α,17α-trihydroxy-16β-methyl-pregnan-20-one 3-acetate 5,17-dipropionate having a melting point of 173°–174° is obtained.

EXAMPLE 9

42 ml of a 3.85 N solution of hydrogen chloride in isopropyl alcohol are added while stirring to a mixture of 6.3 g of 21-chloro-6β-fluoro-3β,5α,17α-trihydroxy-16β-methyl-pregnan-20-one 3-acetate 5,17-dipropionate and 315 ml of methanol. After 3½ hours the mixture is emptied onto saturated sodium bicarbonate solution, the precipitate is taken up in methylene chloride, washed with semi-saturated sodium chloride solution, dried and concentrated by evaporation in vacuo. The resulting 21-chloro-6β-fluoro-3β,5α,17α-trihydroxy-16β-methyl-pregnan-20-one 5,17-dipropionate is dissolved in 42 ml of methylene chloride and 168 ml of acetone and, while stirring and cooling with ice, 6 ml of an 8 N aqueous solution of chromic acid in sulphuric acid are added in the course of 4 minutes. After 30 minutes, a solution of 8.9 g of sodium acetate in 170 ml of water is added dropwise to the mixture which is then extracted several times with methylene chloride. The organic extracts are washed with saturated sodium bicarbonate solution and with sodium chloride solution, dried and concentrated by evaporation in vacuo. After recrystallising from ether, the resulting 21-chloro-6β-fluoro-5α,17α-dihydroxy-16β-methyl-pregnane-3,20-dione 5,17-dipropionate melts at 145°–147°.

EXAMPLE 10

Hydrogen chloride gas is introduced over a period of 5 hours while stirring and cooling with ice into a solution of 100 ml of 21-chloro-6β-fluoro-5α,17α-dihydroxy-16β-methyl-pregnane-3,20-dione 5,17-dipropionate in 10 ml of chloroform. The mixture is emptied onto ice water and extracted with methylene chloride; the extract is washed with a 3% solution of sodium bicarbonate, dried and concentrated by evaporation in vacuo. After recrystallising the residue from methylene chloride/ether, 21-chloro-6α-fluoro-17α-hydroxy-16β-methyl-pregn-4-ene-3,20-dione propionate having a melting point of 235.5°–236° is obtained.

The same compound is also obtained if the 21-chloro-6β-fluoro-5α,17α-dihydroxy-16β-methyl-pregnane-3,20-dione 5,17-dipropionate is first converted, by heating for 9 hours with glacial acetic acid at 80°, into the 21-chloro-6β-fluoro-17α-hydroxy-16β-methyl-pregn-4-ene-3,20-dione propionate having a melting point of 174°–198° and then isomerised with gaseous hydrogen chloride in chloroform in the manner described above to form the above end product.

EXAMPLE 11

(a) Preparation of the hydroxylating micro-organism preparation.

In a 500 ml Erlenmeyer flask, 100 ml of a sterile nutrient solution (containing 1% by weight of yeast extract and 2% by weight of saccharose, pH=5.6) are inoculated with an agar slant culture of Curvularia lunata ATCC 12017 and shaken for 36 hours at 28° and 120 rev/min. 100 ml of a sterile nutrient solution (containing 0.75% (dry weight) of "Corn-steep liquor" and 2% by weight of saccharose, pH=5.5) are inoculated with 5 ml of the resulting culture solution and incubated for 24 hours under the above conditions. The cultivated mycelium is separated off by centrifugation, suspended in an equal volume of a solution of 0.7% by weight of sodium sulphate and 0.02% by weight of Tween 80 ® (Trade name for Polysorbat 80), separated off again by centrifugation and resuspended in half the quantity of the last-mentioned solution.

(b) Transformation and isolation.

Microcrystalline 21-chloro-6α-fluoro-17α-hydroxy-16β-methyl-pregn-4-ene-3,20-dione propionate is suspended in the sodium sulphate Tween 80 solution described above in the ratio of 10 mg steroid/1 ml solution. 1 part by volume of the steroid suspension is added to every 40 parts by volume of the mycelium suspension (see (a)) and the mixture is shaken in the Erlenmeyer flask for 48–96 hours at 28° at 250 rev/min. The resulting culture suspension is extracted several times with ethyl acetate, the crude extract is concentrated by evaporation and the residue is separated by preparative thin layer chromatography [silica gel; mixture of toluene/acetone (8:2)]. Apart from a quantity of regenerated starting material, the conversion product obtained after recrystallising from ether is 21-chloro-6α-fluoro-11β,17α-dihydroxy-16β-methyl-pregn-4-ene-3,20-dione 17-propionate. 360 MHz-NMR spectrum (CDCl₃): 1 (s)-CH₃(18); 1.18(t,J=8.1 Hz)-COCH₂CH₃; 1.39 (d,J=8 Hz)-CH₃(16); 1.44 (s) CH₃(19); 3.95+4.05 (d,J=12 Hz)-CH₂Cl; 4.5 (m)-H(11); 5.1–5.4 (m)-H(6); 6.04 (s)-H(4) [ppm]; m.p. 214°–214.5° C.

EXAMPLE 12

A mixture of 200 mg of 21-chloro-6α-fluoro-11β,17α-dihydroxy-16β-methyl-pregn-4-ene-3,20-dione 17-propionate and 250 mg of 2,3-dichloro-5,6-dicyano-1,4-benzoquinone in 8 ml of dioxan is boiled under reflux for 22.5 hours. 50 ml of a 5% (w/v) aqueous solution of sodium bicarbonate are added to the cooled reaction solution, the mixture is stirred for 30 minutes and extracted with methylene chloride. The organic phase is washed with dilute sodium chloride solution, dried and concentrated in vacuo. The residue is separated by thin layer chromatography on silica gel plates in the system toluene/acetone (4:1). The resulting 21-chloro-6α-fluoro-17β-dihydroxy-16β-methyl-pregna-1,4-diene-3,20-dione 17-propionate is recrystallised from methylene chloride/methanol/ether, melting point 221°–222° C. (decomposition).

EXAMPLE 13

Analogously to Example 12, 200 mg of 21-chloro-6α-fluoro-17α-hydroxy-16β-methyl-pregn-4-ene-3,20-dione propionate (see Example 10) are treated with 250 mg of 2,3-dichloro-5,6-dicyano-1,4-benzoquinone in 8 ml of dioxan and further processed to yield 21-chloro-6α-fluoro-17α-hydroxy-16β-methyl-pregna-1,4-diene-3,20-dione propionate; melting point 216°–219° C. (from methylene chloride/ether).

EXAMPLE 14

An ointment containing 0.1% of 21-chloro-6α-fluoro-11β,17α-dihydroxy-16β-methyl-pregna-1,4-diene-3,20-dione 17-propionate may be prepared as follows:

| Composition (in % by weight) | |
|---|---|
| 21-chloro-6α-fluoro-11β,17-α-dihydroxy-16β-methyl-pregna-1,4-diene-3,20-dione 17 propionate | 0.1% |
| petroleum jelly | 45.0% |
| paraffin oil | 19.6% |
| cetyl alcohol | 5.0% |
| beeswax | 5.0% |
| sorbitan sesquioleate | 5.0% |
| p-hydroxybenzoic acid isopropyl ester | 0.2% |
| perfume | 0.1% |
| water | 20.0% |

The fatty substances and emulsifiers are melted together. The preservative is dissolved in water and the solution is incorporated into the fatty melt by emulsification at an elevated temperature. After cooling, a suspension of the active substance in part of the fatty melt is incorporated into the emulsion and then the perfume is added.

An ointment, containing 0.1% of 21-chloro-6α-fluoro-11β,17α-dihydroxy-16β-methyl-pregn-4-ene-3,20-dione 17-propionate or 0.3% of 21-chloro-6α-fluoro-17α-hydroxy-16β-methyl-pregn-4-ene-3,20-dione propionate or the 1,2-dehydro derivative thereof—in the last two cases the content of paraffin oil is 19.4%—, is also manufactured in an analogous manner.

What is claimed is:
1. A halogenated steroid of the formula

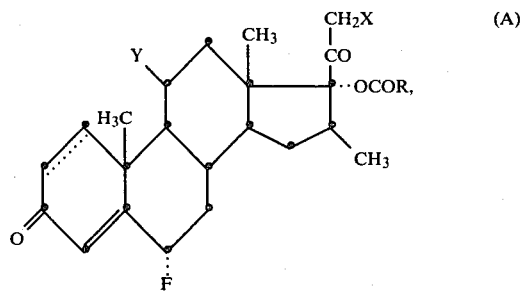

in which
X represents a halogen atom having a maximum atomic number of 17,
Y represents a hydrogen atom or hydroxyl, and
R represents an alkyl radical having a maximum of 6 carbon atoms
and the dotted line in the 1,2-position represents the additional double bond of a 1,2-dehydro derivative.

2. A compound of the formula A according to claim 1 in which Y represents hydroxyl.

3. A compound of the formula A according to claim 1 in which Y represents hydrogen.

4. A compound of the formula A according to claim 1 in which X represents chlorine.

5. A compound of the formula A according to claim 1 in which R represents ethyl.

6. A compound of the formula A according to claim 1 that is saturated in the 1,2-position.

7. 21-chloro-6α-fluoro-11β,17α-dihydroxy-16β-methyl-pregn-4-ene-3,20-dione 17-propionate.

8. 21-chloro-6α-fluoro-17α-hydroxy-16β-methyl-pregn-4-ene-3,20-dione 17-propionate.

9. 21-chloro-6α-fluoro-11β,17α-dihydroxy-16β-methyl-pregna-1,4-diene-3,20-dione 17-propionate.

10. 21-chloro-6α-fluoro-17α-hydroxy-16β-methyl-pregna-1,4-diene-3,20-dione 17-propionate.

11. A pharmaceutical preparation containing one of the compounds defined in claim 1 together with a pharmaceutical carrier.

12. A pharmaceutical preparation containing one of the compounds defined in one of claims 7 to 10 together with a pharmaceutical carrier.

13. Therapeutic method of alleviating or eliminating pathological inflammatory conditions in a warm-blooded animal, characterised by the administration to this warm-blooded animal of a compound according to claim 1 alone or in the form of a pharmaceutical preparation in quantities that are effective in the alleviation or elimination of the inflammation in this warm-blooded animal.

14. Method according to claim 13 in which an inflammation of the skin or mucosa is treated by the topical administration of the active substance.

15. Method according to claim 13 or 14 in which the warm-blooded animal treated is a human being.

16. Process for the manufacture of halogenated steroids of the formula

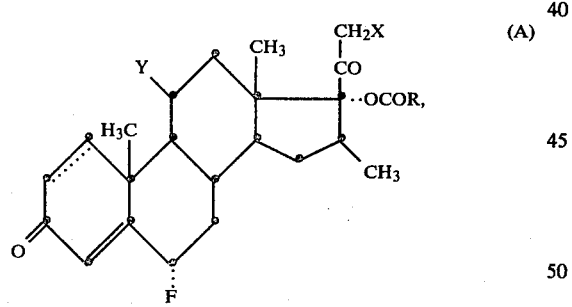

in which
X represents a halogen atom having a maximum atomic number of 17,
Y represents a hydrogen atom or hydroxyl, and
R represents an alkyl radical having a maximum of 6 carbon atoms,
the dotted line in the 1,2-position representing the additional double bond of a 1,2-dehydro derivative, wherein:

(a) 21-(fluoro or chloro)-3β-hydroxy-16-methyl-pregna-5,16-dien-20-one 3-lower alkanoyl ester is treated with a peracid and to form the corresponding 5,6-epimers, which are separated from each other in a resulting mixture of 5,6;16α,17-diepoxides, is treated with hydrogen fluoride, or any obtained 5β,6;16α,17-diepoxide is reacted with a strong oxygen-containing acid, to form the resulting 5α,6β,17α-trihydroxy-16-methylene compound which is then treated with an organic sulphonyl halide in the presence of 2,4,6-collidine or 2,6-lutidine, to form the resulting 5α,6-epoxy-17-α-hydroxy-16-methylene compound, which is then reacted with hydrogen fluoride, to form the corresponding 21-(fluoro or chloro) 6β-fluoro-5α,17α-dihydroxy-3β-lower alkanoyloxy-16-methylene-pregnan-20-one, (c) the resulting 21-(fluoro or chloro)-6β-fluoro-5α,17α-dihydroxy-3βlower alkanoyloxy-16-methylene-pregnan-20-one, the two free hydroxyl groups are esterified by a lower alkanecarboxylic acid, (d) the resulting 21-(fluoro or chloro)-6β-fluoro-3β,5α,17α-trihydroxy-16-methylene-pregnan-20-one 3-lower alkanoyl-5,17-di-lower alkanecarbonyl ester is catalytically hydrogenated, (e) the resulting 21-(fluoro or chloro)-6β-fluoro-3β,5α,-17α-trihydroxy-16β-methyl-pregnan-20-one 3-lower alkanoyl-5,17-di-lower alkanecarbonyl ester, the esterified 3-hydroxyl group is freed by selective hydrolysis and subsequently oxidised into the 3-oxo group, (f) the resulting 21-(fluoro or chloro)-6β-fluoro-5α,17α-di-lower alkanecarbonyloxy-16β-methyl-pregnane-3,20-dione is treated with an acid in order to remove the 5-positioned lower alkanecarbonyloxy group and, with or without converting any resulting compound having 6β-fluoro, by catalytic treatment with a strong acid, into the 6α-fluoro isomer, and, where Y represents hydroxyl, the resulting end product of the formula A in which Y represents hydrogen is hydroxylated in the 11β-position by means of the enzymatic system of a 11β-hydroxylating micro-organism, and where the compound of formula A is a 1,2-dehydro compound the resulting 1,2-saturated end product of the formula A is dehydrogenated.

17. Process according to claim 16, wherein the starting material of step (a) is 21-(fluoro or chloro)-3β-hydroxy-16β-methyl-pregna-5,16-dien-20-one 3-formate, obtained by reacting 3β-hydroxy-16-methylpregna-5,16-dien-20-one or a carboxylic acid ester thereof with a lower alkyl oxalate or formate in the presence of an alkali metal lower alcoholate, converting the resulting 21-(lower alkoxalyl or formyl)-5,16-dien-20-one derivative into 21-diazo-3β-hydroxy-16-methylpregna-5,16-dien-20-one by reacting with an organic sulphonylazide, treating the diazo-derivative with hydrogen fluoride or hydrogen chloride, and esterifying the resulting 21-(fluoro or chloro)-3β-hydroxy-16-methyl-pregna-5,16-dien-20-one with 85% aqueous formic acid.

18. Process according to claim 16, wherein the starting material of step (a) is 21-(fluoro or chloro)-3β-hydroxy-16β-methyl-pregna-5,16-dien-20-one 3-acetate, obtained by reacting 3β-hydroxy-16-methylpregna-5,16-dien-20-one or a 3-carboxylic acid ester thereof with a lower alkyl oxalate or formate in the presence of an alkali metal lower alcoholate, converting the resulting 21-(lower alkoxalyl or formyl)-5,16-dien-20-one derivative into 21-diazo-3β-hydroxy-16-methylpregna-5,16-dien-20-one by reacting with an organic sulphonylazide, treating the diazo-derivative with hydrogen fluoride or hydrogen chloride, and esterifying the resulting 21-(fluoro or chloro)-3β-hydroxy-16-methylpregna-5,16-dien-20-one with acetic anhydride in 2,4,6-collidine or 2,6-lutidine.

19. Process according to claim 16, wherein in carrying out process stage (e), the 21-(chloro or fluoro)-6β-fluoro-3β,5α,17α-trihydroxy-16β-methylpregnan-20-one 3-formate-5,17-di-lower alkanecarbonyl ester is hydrolysed with an alkali metal hydrogen carbonate at room temperature.

20. Process according to claim 16, wherein, in carrying out process stage (e), a 21-(chloro or fluoro)-6β-fluoro-3β,5α,17α-trihydroxy-16β-methylpregnan-20-one 3-lower alkanoyl-5,17-di-lower alkanecarbonyl ester is hydrolyzed with a strong acid in one or more alkanols.

21. Process according to claim 18, wherein in carrying out process stage (e), a 21-(chloro or fluoro)-6β-fluoro-3β-5α,17α-trihydroxy-16β-methylpregnan-20-one 5,17-di-lower alkanecarbonyl ester is oxidized with a compound of hexavalent chromium.

22. Process according to claim 16, wherein in stage (c), the two free hydroxyl groups in the 21-(fluoro or chloro)-6β-fluoro-5α,17α-dihydroxy-3β-lower alkanoyloxy-16-methylene-pregnan-20-one are esterified by treatment with a mixed anhydride of a lower alkanecarboxylic acid with trifluoroacetic acid.

23. Process according to claim 16, wherein platinum is used as the hydrogenation catalyst in stage (d).

24. Process according to claim 16, wherein in process stage (e), a 21-(fluoro or chloro)-6β-fluoro-3β,5α,17α-trihydroxy-16β-methyl-pregnan-20-one 5,17-di-lower alkanecarbonyl ester ioxidized with a solution of chromium trioxide in aqueous sulphuric acid, in acetone.

25. Process according to claim 16, wherein in order to carry out both steps of the process stage (f) simultaneously, a 21-(fluoro or chloro)-6β-fluoro-5α,17α-di-lower alkanecarbonyloxy-16β-methyl-pregn-a-one-3,20-dione is treated with anhydrous hydrogen chloride or hydrogen bromide in a halogenated hydrocarbon.

26. Process according to claim 16, wherein the biological 11β-hydroxylation is carried out with the 11β-hydroxylating enzyme system of *Curvularia lunata* in a growing or static culture.

27. Process according to claim 16, wherein dehydrogenation is effected with 2,3-dichloro-5,6-dicyano-1,4-benzoquinone.

28. Process according to claim 16, wherein, carrying out, additionally, the optional step of the microbial 11β-hydroxylation, a compound of the formula A is manufactured in which Y represents hydroxyl.

29. Process according to claim 16, wherein a compound of the formula A is manufactured in which Y represents hydrogen.

30. Process according to claim 16, wherein, employing 3β-lower alkanoyloxy-21-chloro-16-methylpregna-5,16-dien-20-one as starting material, a compound of the formula A is manufactured in which X represents chlorine.

31. Process according to claim 16, wherein, esterifying with a derivative of propionic acid on stage (c) a compound of the formula A is manufactured in which R represents ethyl.

32. Process according to claim 16, wherein a compound of the formula A is manufactured that is saturated in the 1,2-position.

33. Process according to claim 16, wherein employing 3β-lower alkanoyloxy-21-chloro-16-methylpregna-5,16-dien-2-one as starting material, esterifying with a derivative of propionic acid in state (c) and carrying out, additionally, the optional step of the microbial 11β-hydroxylation, 21-chloro-6α-fluoro-11β,17α-dihydroxy-16β-methyl-pregn-4-ene-3,20-dione 17-propionate is manufactured.

34. Process according to claim 16, wherein, employing 3β-lower alkanoyloxy-21-chloro-16-methylpregna-5,16-dien-20-one as starting material and esterifying with a derivative of propionic acid in stage (c), 21-chloro-6α-fluoro-17α-hydroxy-16β-methyl-pregn-4-ene-3,20-dione 17-propionate is manufactured.

35. Process according to claim 16, wherein, employing 3β-lower alkanoyloxy-21-chloro-16-methylpregna-5,16-dien-20-one as starting material, esterifying with a derivative of propionic acid in stage (c), and in any sequence carrying out, additionally, the optional step of the microbial 11β-hydroxylation and 21-chloro-6α-fluoro-11β,17α-dihydroxy-16β-methyl-pregna-1,4-diene-3,20-dione 17-propionate is manufactured.

36. Process according to claim 16, wherein employing 3β-lower alkanoyloxy-21-chloro-16-methylpregna-5,16-dien-2-one as starting material, esterifying with a derivative of propionic acid in stage (c), and carrying out the additional optional step of 1,2-dehydrogenation, 21-chloro-6α-fluoro-17α-hydroxy-16β-methyl-pregna-1,4-diene-3,20-dione 17-propionate is manufactured.

* * * * *